(12) United States Patent
Mou et al.

(10) Patent No.: US 10,883,974 B2
(45) Date of Patent: Jan. 5, 2021

(54) METHOD FOR PROVIDING AIR QUALITY INFORMATION

(71) Applicant: Microjet Technology Co., Ltd., Hsinchu (TW)

(72) Inventors: Hao-Jan Mou, Hsinchu (TW); Ta-Wei Hsueh, Hsinchu (TW); Li-Pang Mo, Hsinchu (TW); Shih-Chang Chen, Hsinchu (TW); Ching-Sung Lin, Hsinchu (TW); Chi-Feng Huang, Hsinchu (TW); Yung-Lung Han, Hsinchu (TW); Hsuan-Kai Chen, Hsinchu (TW); Wei-Ming Lee, Hsinchu (TW); Chang-Yen Tsai, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 338 days.

(21) Appl. No.: 16/025,051

(22) Filed: Jul. 2, 2018

(65) Prior Publication Data

US 2019/0033278 A1    Jan. 31, 2019

(30) Foreign Application Priority Data

Jul. 27, 2017  (TW) .............................. 106125340 A
Jul. 27, 2017  (TW) .............................. 106125342 A

(51) Int. Cl.
*G01N 33/00* (2006.01)
*G06Q 10/06* (2012.01)
(Continued)

(52) U.S. Cl.
CPC ..... *G01N 33/0062* (2013.01); *G01C 21/3461* (2013.01); *G01N 33/0004* (2013.01);
(Continued)

(58) Field of Classification Search
CPC ........... G01N 33/0062; G01N 33/0047; G01N 2033/0068; G01N 33/00; G01N 33/004;
(Continued)

(56) References Cited

U.S. PATENT DOCUMENTS

2003/0093484 A1    5/2003  Petite
2009/0309744 A1   12/2009  Fu et al.
(Continued)

FOREIGN PATENT DOCUMENTS

CN      103412086 A    11/2013
CN      104061962 A     9/2014
(Continued)

OTHER PUBLICATIONS

National Research Council (US) Committee on Airliner Cabin Air Quality. The Airliner Cabin Environment: Air Quality and Safety. Washington (DC): National Academies Press (US); 1986. 4, Air Quality in Emergency Situations. Available from: https://www.ncbi.nlm.nih.gov/books/NBK219005/ (Year: 1986).*
(Continued)

*Primary Examiner* — Mischita L Henson
(74) *Attorney, Agent, or Firm* — Birch, Stewart, Kolash & Birch, LLP

(57) ABSTRACT

A method for providing air quality information is disclosed. The method includes steps of collecting single-point air quality data from a plurality of mobile devices in a predetermined period of time, wherein the single-point air quality data is sensed by an actuating and sensing module of the mobile device and transmitted to a cloud data processing device through communication transmission. The single-point air quality data is combined with geographic information and processed to generate a real-time air quality map by the cloud data processing device. After the cloud data processing device receives a current location from a client
(Continued)

device through communication transmission, information including a motion direction, a designated route, air quality information related to the current location, abnormal-air-quality notification or an evacuated route is transmitted to the client device.

19 Claims, 4 Drawing Sheets

(51) Int. Cl.
  *G01C 21/34* (2006.01)
  *G08B 21/12* (2006.01)
  *G01P 13/00* (2006.01)
  *G01W 1/02* (2006.01)
  *G08B 27/00* (2006.01)

(52) U.S. Cl.
  CPC ...... *G01N 33/0047* (2013.01); *G01P 13/0006* (2013.01); *G01W 1/02* (2013.01); *G06Q 10/06* (2013.01); *G08B 21/12* (2013.01); *G01N 2033/0068* (2013.01); *G08B 27/005* (2013.01); *G08B 27/006* (2013.01)

(58) Field of Classification Search
  CPC ........... G01N 33/0042; G01N 33/0037; G01N 33/0039; G01N 33/0054; G06Q 10/06; G01P 13/0006; G01P 13/00; G01W 1/02; G01C 21/3461; G08B 21/12; G08B 27/005; G08B 27/006
  See application file for complete search history.

(56) References Cited

U.S. PATENT DOCUMENTS

| | | | | |
|---|---|---|---|---|
| 2010/0118149 | A1* | 5/2010 | Levin | G06Q 10/06 348/169 |
| 2013/0174646 | A1* | 7/2013 | Martin | F24F 11/30 73/31.02 |
| 2015/0330817 | A1* | 11/2015 | Law | G01N 33/0073 702/3 |
| 2016/0318368 | A1 | 11/2016 | Alger et al. | |
| 2018/0017536 | A1* | 1/2018 | Le Neel | G01N 33/0047 |
| 2018/0346130 | A1* | 12/2018 | Jouper | G01N 33/004 |

FOREIGN PATENT DOCUMENTS

| | | | |
|---|---|---|---|
| CN | 104395780 | A | 3/2015 |
| CN | 104697539 | A | 6/2015 |
| CN | 104820072 | A | 8/2015 |
| CN | 104950076 | A | 9/2015 |
| CN | 105043401 | A | 11/2015 |
| CN | 103529167 | B | 3/2016 |
| TW | 200821977 | A | 5/2008 |
| TW | 200951888 | A | 12/2009 |
| TW | M525446 | U | 7/2016 |
| TW | M538580 | U | 3/2017 |
| TW | M538593 | U | 3/2017 |
| WO | WO 2017/11470 | A1 | 7/2017 |

OTHER PUBLICATIONS

David Gray, What are point clouds? 5 easy facts that explain point clouds, 2020, https://info.vercator.com/blog/what-are-point-clouds-5-easy-facts-that-explain-point-clouds, Accessed online Jul. 29, 2020 (Year: 2020).*

Chien et al., "A study of relationship among the suspended particles and meteorological factors at downstream of Jhuoshei River." Journal of Soil and Water Conservation, vol. 44, No. 4, 2012, pp. 391-406, with abstract.

Taiwanese Office Action and Search Report for Taiwanese Application No. 106125340, dated Nov. 25, 2019.

Extended European Search Report, dated Sep. 13, 2018, for European Application No. 18180923.7.

* cited by examiner

METHOD FOR PROVIDING AIR QUALITY INFORMATION

FIELD OF THE INVENTION

The present disclosure relates to a data processing method for a specific service, and more particularly to a method for providing air quality information by collecting air detection data from a plurality of mobile devices and computing the air detection data to generate air quality information and provides the air quality information to client terminals.

BACKGROUND OF THE INVENTION

Nowadays, the air pollution problems are becoming increasingly serious in Taiwan and its neighboring regions. In particular, the concentration of fine suspended particles (PM 2.5) is often too high, and the public gradually develops habits of accessing real-time air quality monitoring data online at any time in daily life, so as to make immediate protective measures against the air pollution. Taking the air quality monitoring network of the Environmental Protection Agency of the Executive Yuan as an example, the current air quality monitoring system utilizes the air quality monitoring stations established throughout the country to sample and analyze the air, and the monitored data from the fixed-point monitoring stations are integrated as an air quality index (AQI) to quantitatively describe the air quality and be published on the website for public inspection.

However, the fixed-point monitoring method includes the following disadvantages. Firstly, since the construction cost of the monitoring stations is very expensive, the established number is limited. As so, the fixed-point monitoring stations can provide the air quality measured at the specific locations and the place surrounding the specific area merely, instead of the entire area covering all users' locations completely. Furthermore, the users cannot obtain the precise air quality data based on their own locations. In addition, when the AQI index of a specific area reaches a level representing harmful to human health, the air quality monitoring network only provides the users located in that area with a suggestion to avoid going out from the buildings, but does not provide further useful information to facilitate the users to deal with the poor air quality.

In order to overcome the drawbacks of the fixed-point monitoring method for the air quality, Taiwan patent application with the publication number TW 201719540 discloses a cloud-based sharing method with positioning and air detecting functions, wherein a handheld mobile device is combined with an air sensing unit. In this way, the handheld mobile device can be used to position a specific location and simultaneously sense the air quality at the specific location. Then, the handheld mobile device uploads the positioning result and the air quality sensing result to a cloud data processing platform as well as marking the air quality sensing result associating with the corresponding location on a social platform. The cloud data processing platform compares and analyzes the measured air quality data with an air database. If the analyzed results indicate that the measured air quality fails to meet an acceptable standard, the cloud data processing platform will send out a message to inform the relevant units to carry out maintenance and provide the analyzed results to other users for reference.

However, the above methods only deal with the single information generated by the individual handheld mobile devices, but does not integrate the air quality data sensed by the plural handheld mobile devices at different locations. Furthermore, the air quality data is not merged with the other types of data information to generate more valuable derivative information for users' reference. At the same time, the method of the patent application evaluates the level of air quality merely, but does not specify other possible forms and contents of the analyzed results. In addition, there is no practical embodiment or structure of the air sensing unit mentioned in the specification of the patent application.

Therefore, there is a need of providing a method for providing air quality information to solve the drawbacks in prior arts.

SUMMARY OF THE INVENTION

Since the current air quality monitoring system samples the air and senses the quality of the air through configuration of the fixed-point stations, the sensed air quality data cannot include the air quality information at all users' locations. Another conventional opinion is to combine a handheld mobile device with an air sensing unit, so that the air quality can be sensed at anytime and in anywhere. However, there is a lack of integration and utilization of the air quality data collected at different time and in different place, and there is no relevant data combined to generate the derivative information with additional benefits for users. Moreover, the users cannot actively search for the air quality information related to specific locations. Therefore, the prior art fails to effectively exert the value of the air quality data sensed by the handheld mobile devices. In addition, the prior art does not tend to improve the air sensing unit. Hence, when the air sensing unit is applied to a handheld mobile device and sensed during a motion, the accuracy of the sensing result is really questionable.

In order to solve the above problems, the present disclosure provides a plurality of mobile devices each of which has an actuating and sensing module, the mobile devices sense a plurality of single-point air quality data at their respective locations and transmit the sensed single-point air quality data to a cloud data processing device. The cloud data processing device collects the single-point air quality data from the mobile devices in a predetermined period of time, then integrating and calculating the single-point air quality data to generate a calculation result. Afterwards, the cloud data processing device combines the calculation result with geographic information to generate a real-time air quality map. At this time, a client device can transmit a current location to the cloud data processing device through communication transmission and send a request for information to the cloud data processing device. The cloud data processing device generates the information based on the real-time air quality map and the current location, and transmits the information to the client device.

In contrast to the prior art, the present disclosure provides a system combining the air quality data from a plurality of mobile devices and integrating other relevant data to produce a real-time air quality map. In this way, it not only makes full use of the advantages of the number and mobility of the mobile devices, but also makes the information more accurate than that of the conventional fixed-point air monitoring system. In addition, since the processed single-point air quality data of the present disclosure are further combined with the geographic information and the meteorological data, a variety of derivative information beneficial to the user can be generated. Such derivative information includes a designated route, air quality information related to a specified location, an abnormal-air-quality notification, a warning notification, or an evacuation route. As to the prior art, the air quality information are determined by simple data from fixed point locations, and it fails to provide users with the ability to actively query the air quality related to a specific location. In comparison, the present disclosure better utilizes the information with big data operations and has significant improvement in providing precise instant air quality information related to a specified location.

In accordance with an aspect of the present disclosure, there is provided a system for providing air quality information. The system includes a plurality of mobile devices, a cloud data processing device and a client device. Each mobile device includes a positioning module and an actuating and sensing module. The actuating and sensing module includes an actuating device and a sensor. The actuating device actuates air from the external environment into the inner of the actuating and sensing module, and the sensor senses the air to generate the air detection data. The positioning module of the mobile device generates position data according to a location of the mobile device. Each mobile device, at a predetermined time, generates the air detection data by the actuating and sensing module and generates the position data by the positioning module, after which the air detection data and the position data is combined to generate the single-point air quality data. In contrast to the prior art, the mobile device of the present disclosure provides the actuating and sensing module to actuate the air from the external environment into the inner for sensing, which facilities the mobile device to provide a better adaptability in moving situation. That is, the air quality is ensured to be sensed accurately while the mobile device is moving.

In accordance with another aspect of the present disclosure, there is provided a method for providing air quality information. The method includes collecting single-point air quality data from a plurality of mobile devices, respectively, in a predetermined period of time, wherein the single-point air quality data is sensed by an actuating and sensing module of each mobile device and transmitted to a cloud data processing device through communication transmission. Then, the single-point air quality data is integrated and calculated by the cloud data processing device to obtain a calculation result. The cloud data processing device generates a real-time air quality map by combining the calculation result and geographic information. Once the cloud data processing device receives a current location data through communication transmission, the cloud data processing device generates information based on the current location and the real-time air quality map, and transmits the information to the client device through the communication transmission.

In accordance with other aspect of the present disclosure, there is provided a method for providing air quality information. The method includes collecting single-point air quality data from a plurality of mobile devices, respectively, in a predetermined period of time, wherein the single-point air quality data is sensed by an actuating and sensing module of each mobile device and transmitted to a cloud data processing device through communication transmission. Then, the single-point air quality data is integrated and calculated by the cloud data processing device to obtain a calculation result. The cloud data processing device generates an updated real-time air quality map by combining the calculation result with geographic information and meteorological data, wherein the meteorology data includes at least one selected from the group consisting of a wind direction, a wind speed, a humidity, a temperature, a weather pattern and a combination thereof. Once the cloud data processing device receives a current location through communication transmission, the cloud data processing device generates information based on the current location and the real-time air quality map, and transmits the information to the client device through the communication transmission.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
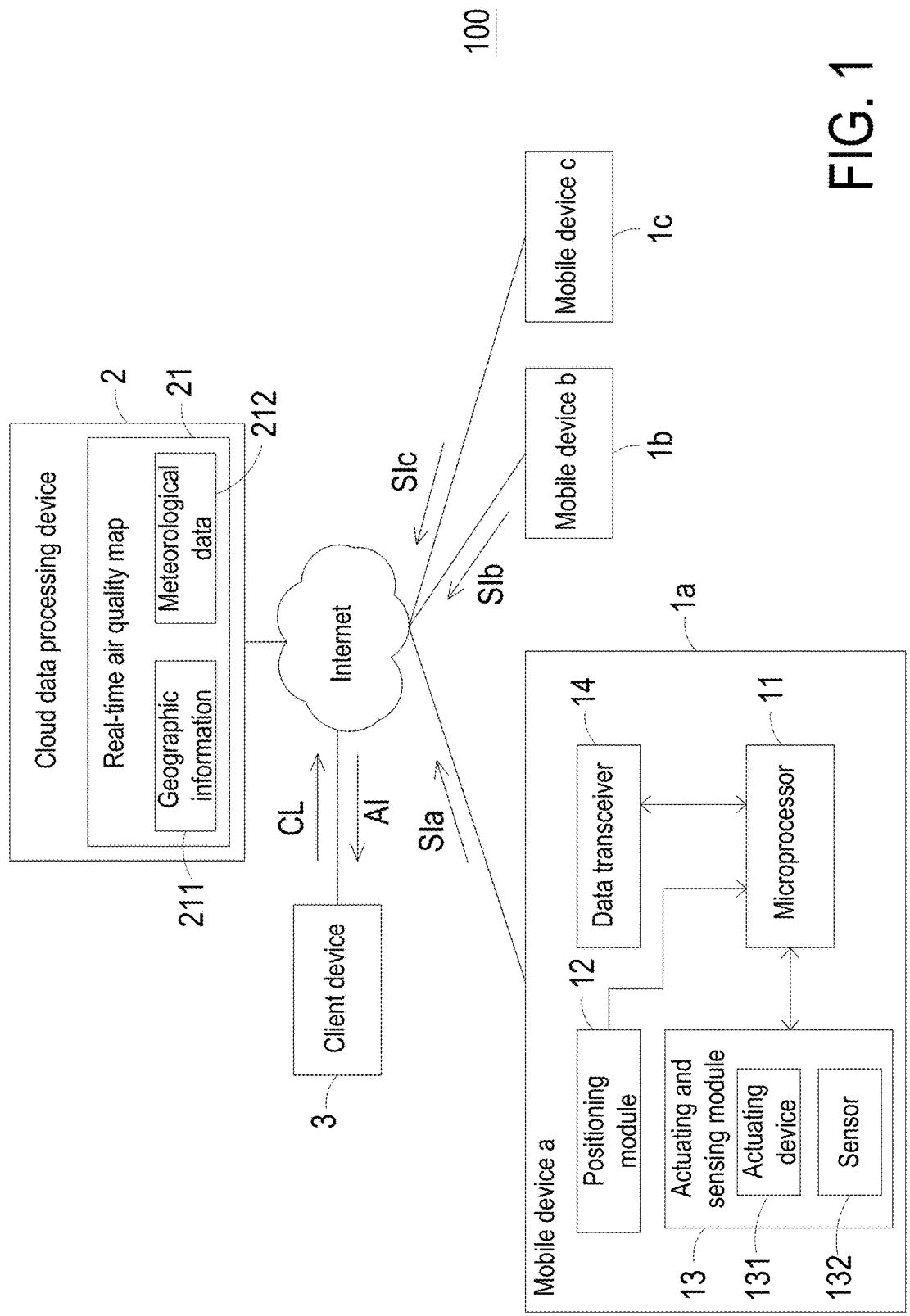
FIG. 1 is a block diagram illustrating a system for providing an air quality information according to an embodiment of the present disclosure.

Please refer to FIG. 1. The present discourse provides a method for providing air quality information, and the method is applied to a system 100 including at least one cloud data processing device 2, at least one predetermined period of time, at least one actuating and sensing module 13, at least one mobile device 1a, at least one generated real-time air quality map, at least one client device 3, and at least one current location. The number of the cloud data processing device 2, the predetermined period of time, the actuating and sensing module 13, the mobile device 1a, the real-time air quality map, the client device 3, and the current location is exemplified by one for each in the following embodiments but not limited thereto. It is noted that each of the cloud data processing device 2, the predetermined period of time, the actuating and sensing module 13, the mobile device 1a, the real-time air quality map, the client device 3, and the current location can also be provided in plural numbers.

Please refer to FIG. 1, which is a block diagram illustrating a system for providing air quality information according to an embodiment of the present disclosure. The system 100 for providing the air quality information includes a plurality of mobile devices 1a, 1b and 1c, a cloud data processing device 2, and a client device 3. The mobile devices 1a, 1b and 1c may have same structure and can be for example but not limited to a mobile phone, a tablet, a wearable device, or any similar mobile electronic device constructed to contain a microprocessor, a RAM, and other components. The mobile device 1a is taken as an example for further describing the structure of the mobile device 1a, 1b and 1c in the following. As shown in FIG. 1, the mobile device 1a includes a microprocessor 11, a positioning module 12, an actuating and sensing module 13 and a data transceiver 14. The microprocessor 11 is electrically connected to the positioning module 12, the actuating and sensing module 13 and the data transceiver 14. The positioning module 12 can be a GPS satellite positioning module, but not limited thereto.

The actuating and sensing module 13 includes an actuating device 131 and a sensor 132. The actuating device 131 is a driver capable of driving a controlled system in response to a control signal. The function of the actuating device 131 is to drive air from the external environment, so that the air is introduced into the interior of the actuating and sensing module 13. The actuating device 131 can include an electric actuator, a magnetic actuator, a thermal actuator, a piezoelectric actuator, and a fluid actuator. For example, it can be an electric actuator such as an AC-DC motor or a stepping motor, a magnetic actuator such as a magnetic coil motor, a thermal actuator such as a heat pump, a piezoelectric actuator such as a piezoelectric pump, or a fluid actuator such as a gas pump and a liquid pump, but is not limited thereto.

The sensor 132 is disposed adjacent to the actuating device 131 for detecting at least one detecting target in the air introduced by the actuating device 131 and generating corresponding air detection data. The sensor 132 can include a sensor such as a temperature sensor, a volatile organic compound sensor (for example, a sensor for sensing the formaldehyde and the ammonia), a particulate sensor (for example, a PM 2.5 particle sensor), a carbon monoxide sensor, a carbon dioxide sensor, an oxygen sensor, an ozone sensor, other gas sensors, a humidity sensor, a moisture sensor, a measuring sensor used for measuring the compounds and/or biological substances in water, other liquids or air (for example, a water quality sensor), other liquid sensors, a light sensor used for measuring the environment, or a group formed by any combination of the above-mentioned sensors, but is not limited thereto. Therefore, the detecting target of the sensor 132 can be volatile organic gas such as ammonia or ethanol, or the detecting target can also be carbon monoxide, carbon dioxide, sulfur dioxide, nitrogen dioxide, suspended particle, fine suspended particle, oxygen, ozone or any combination of the above-mentioned substances. Moreover, the sensor 132 can sense a virus, a bacterium or a microorganism, by a direct or indirect method, but is not limited thereto.

The client device 3 can be a mobile phone, a tablet computer or a wearable device, which includes a GPS satellite positioning function and a communication transmission module, or can be any mobile electronic device constructed to include components such as a microprocessor and a RAM, but is not limited thereto. In some embodiments, the client device 3 is one of the plurality of mobile devices 1*a*, 1*b* and 1*c*.

The cloud data processing device 2 is a computer or any similar device constructed to include CPU, RAM, and etc., and have a data analysis management function. In the system 100, the cloud data processing device 2 serves as a server to connect the mobile device 1*a*, 1*b* and 1*c* and the client device 3 through the internet, so as to transmit and receive the information through a wired or wireless manner of communication transmission. The wired manner of communication transmission can be carried out by utilizing a RS485 communication port, an RS232 communication port, a Modbus communication port or a KNX communication port. The wireless manner of communication transmission can be carried out by utilizing a Zigbee communication technology, a Z-wave communication technology, an RF communication technology, a Bluetooth communication technology, a Wifi communication technology or an EnOcean communication technology. Oppositely, the data transceiver 14 of the mobile device 1*a* can also be a module to which the above-mentioned communication transmission technology is applied.

Figure 2:
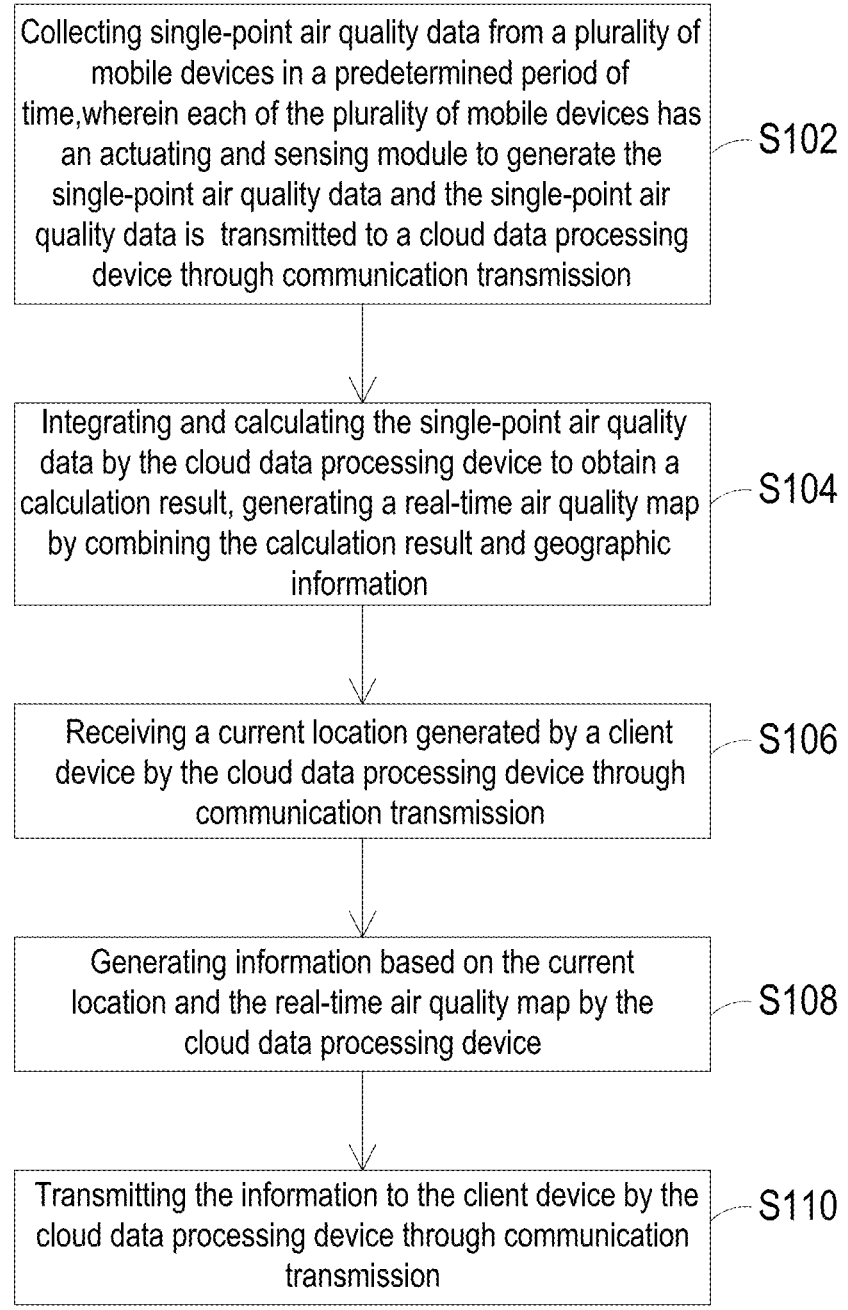
FIG. 2 is a flow chart illustrating a method of providing an air quality information according to a first embodiment of the present disclosure.

Please refer to FIGS. 1 and 2. FIG. 2 is a flow chart illustrating a method of providing air quality information according to a first embodiment of the present disclosure. In the embodiment, at the step S102, the cloud data processing device 2 collects single-point air quality data SIa, SIb and SIc in a predetermined period of time. The cloud data processing device 2 may perform the collecting operation on a periodic basis at regular intervals, e.g., at intervals of 5 minutes or of 1 hour. That is, the single-point air quality data SIa, SIb and SIc is generated by the mobile devices 1*a*, 1*b* and 1 *c* at the predetermined time, respectively. Taking the mobile device 1*a* as an example, the user can pre-set the positioning module 12 to automatically generate position data at specific time regularly, or manually request the positioning module 12 to generate the position data at designated time. The position data can be a coordinate location positioned by the GPS satellite positioning system for the mobile device 1*a* and may include a timestamp. As the position data is generated, the actuating and sensing module 13 of the mobile device 1*a* is synchronously in action, sucking air from the external environment and generating the air detection data by sensing the sucked air. The microprocessor 11 receives the position data from the positioning module 12 and the air detection data from the actuating and sensing module 13, respectively, and accordingly generates the single-point air quality data SIa. Since the position data contains the timestamp, which identifies when the position coordinate is generated, the single-point air quality data SIa also retains the timestamp to have such time record. Therefore, the single-point air quality data SIa contains a coordinate location of the mobile device 1*a* at a specific time as well as air detection data obtained in that coordinate location. After the data transceiver 14 receives the single-point air quality data SIa from the microprocessor 11, the data transceiver 14 transmits the single-point air quality data SIa to the cloud data processing device 2 through communication transmission.

In the step S104, the cloud data processing device 2 integrates and calculates the single-point air quality data SIa, SIb and SIc transmitted from the mobile devices 1*a*, 1*b* and 1 *c*, and generates a calculation result. The single-point air quality data SIa, SIb, and SIc might be generated by the mobile devices 1*a*, 1*b* and 1 *c* at any time in between one of the intervals at which the cloud data processing device 2 performs the collecting operation. For instance, if the cloud data processing device 2 is set to perform the collecting operation in every 10 minutes, and the time recorded by the timestamps in the single-point air quality data SIa, SIb and Sic is in between one a 10-minute interval which is between the last collecting operation and the about-to-be-performed collecting operation of the cloud data processing device 2, the cloud data processing device 2 determines the single-point air quality data SIa, SIb and Sic as a same batch of air detection data fetched at the same particular period of time, and processes the single-point air quality data SIa, SIb and SIc together to generate the calculation result.

The cloud data processing device 2 combines the above-mentioned calculation result with geographic information 211 to generate a real-time air quality map 21 providing all the acquired single-point air quality data SIa, Sib and SIc in the particular period of time. Furthermore, the cloud data processing device 2 may connect to a meteorological center to fetch instant meteorological data 212, and combine the meteorological data 212 with the above-mentioned calculation result to generate an updated real-time quality map 21. The meteorological data can include at least one selected from the group consisting of a wind direction, a wind speed, a humidity, a temperature, a weather pattern or a combination thereof. In some embodiments, if there is no corresponding air quality information related to a specific location, the cloud data processing device 2 fetches the air quality information of the other locations neighboring to the specific location and calculates an average thereof. To simulate more precisely, the average is further calculated with using the meteorological data 212 as a parameter, and the calculation result will be presented as the air quality information related to the specific location. In such way, when the number of mobile devices 1a, 1b, and 1c reaches a certain scale, through the big data operations of the cloud data processing device 2, the real-time air quality map 21 can provide much higher precision than the conventional fixed-point monitoring stations since the data sources spread over a large area with high density.

In the step S106, the client device 3 generates data of a current location CL. The user is allowed to download a mobile application (hereinafter abbreviated as APP), which requires the user to enable the data access permission of the GPS positioning module of the client device 3. If the user agrees with the request, a coordinate location sensed by the GPS positioning module is automatically designated as the current location CL and uploaded to the cloud data processing device 2 when the client device 3 is turned on or when the APP is activated, optionally. Alternatively, the user can manually operate the APP to generate the current location CL and upload it to the cloud data processing device 2. In this way, the current location CL might be a GPS coordinate location where the user device 3 is located, or the current location CL might be a specific location (where is not the location of the client device 3) inputted and designated by the user.

In the step S108, the cloud data processing device 2 receives the current location CL, and generates information AI based on the real-time air quality map 21 and the current location CL. The information AI may be air quality information related to the current location CL, e.g., a concentration of the pollutant such as suspended particles, but not limited thereto. Then, in the step S110, the cloud data processing device 2 transmits the information AI (e.g., the air quality information) to the client device 3. The client device 3 displays the air quality information on the display (not shown) via a user interface design.

In another embodiment of the present disclosure, the current location CL mentioned in the step S106 is a GPS coordinate location of the client device 3, and the information AI generated based on the real-time air quality map and the current location CL, which is mentioned in the step S108, further includes a motion direction. The client device 3 displays the motion direction on the display (not shown) via a user interface design, thereby informing the user the direction toward the area with good air quality, as a recommended reference for the daily schedule of the user.

Figure 3:
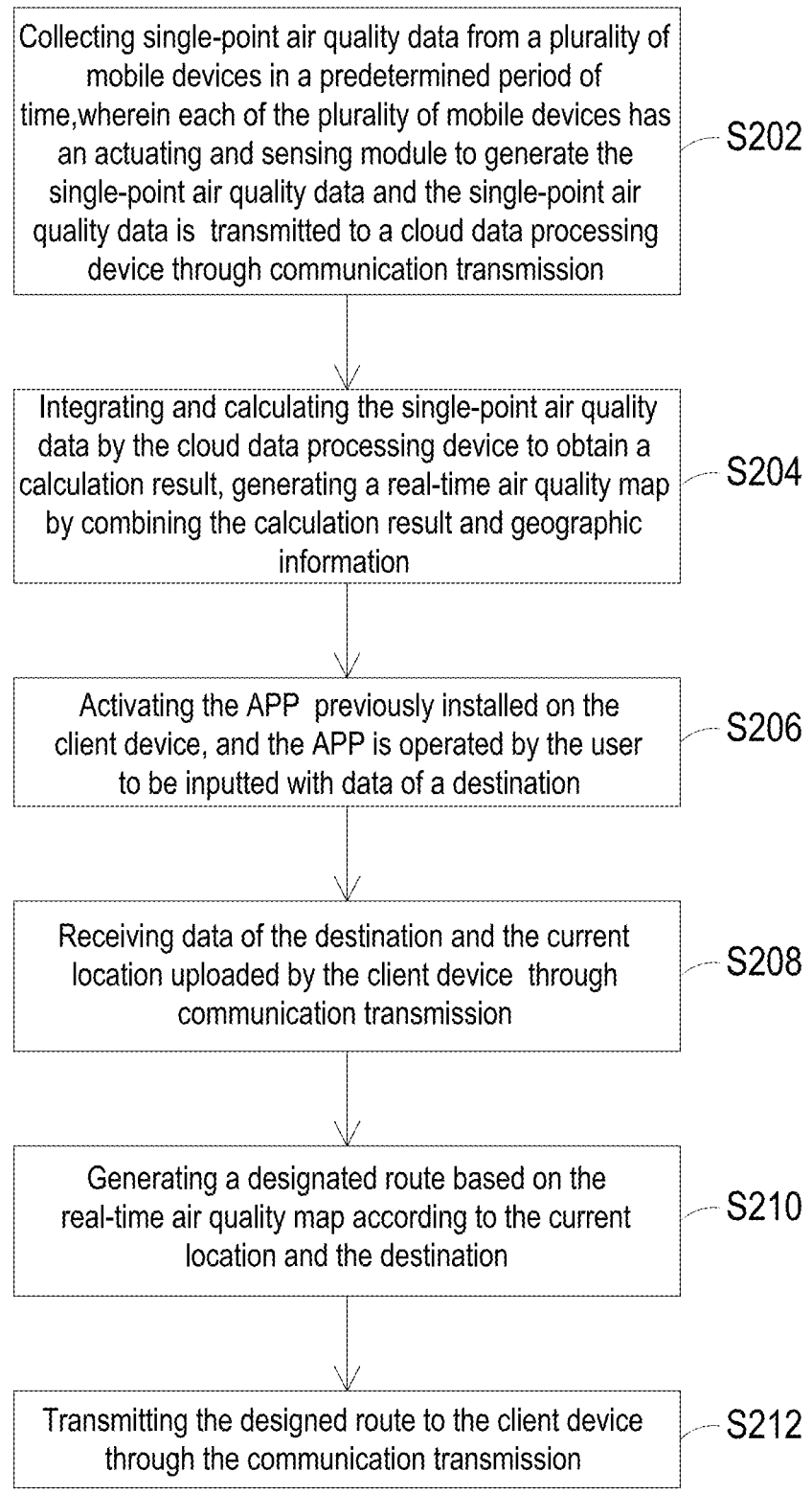
FIG. 3 is a flow chart illustrating a method of providing an air quality information according to a second embodiment of the present disclosure.

Please refer to FIGS. 1 and 3 together. FIG. 3 is a flow chart illustrating a method of providing air quality information according to a second embodiment of the present disclosure. In this embodiment, the steps S202 and S204 are similar to the steps S102 and S104 of the previous embodiment, and will not be redundantly described herein. Being different from the first embodiment, in the step S206, the client device 3 activates the APP which is previously installed thereon, and the APP is operated by the user to be inputted with data of a destination. At the same time, the client device 3 detects the GPS coordinate location thereof to generate the current location CL. In the step S208, the cloud data processing device 2 receives data of the destination and the current location CL uploaded by the client device 3 through communication transmission. In the step S210, the cloud data processing device 2 generates a designated route based on the real-time air quality map 21 according to the current location CL and the destination. The designated route is a path from the current location CL toward the destination. In the step S212, the cloud data processing device 2 transmits the designed route to the client device 3 through the communication transmission, and displays the designated route on the display (not shown) via a user interface design. Through the above steps, the cloud data processing device 2 calculates to generate the designated route based on the updated real-time air quality map 21, which is constructed by combining the collected single-point air quality data SIa, SIb and SIc with the meteorological data such as a wind direction or a weather pattern, so as to instruct the user to avoid the areas where the air quality may be poor on the way to their desired destination.

Figure 4:
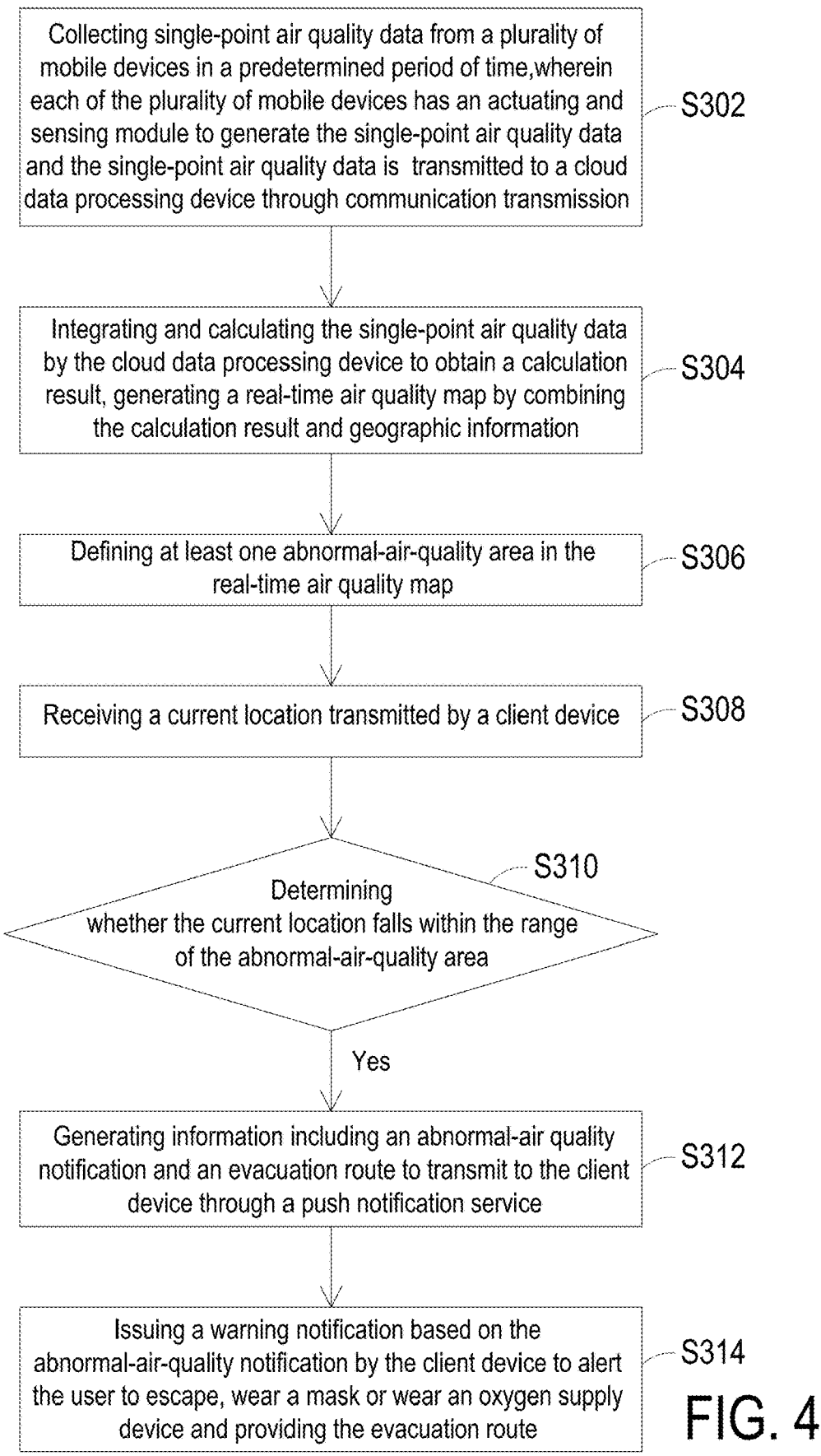
FIG. 4 is a flow chart illustrating a method of providing an air quality information according to a third embodiment of the present disclosure.

Please refer to FIGS. 1 and 4 together. FIG. 4 is a flow chart illustrating a method of providing air quality information according to a third embodiment of the present disclosure. In this embodiment, the steps S302 and S304 are similar to the steps S102 and S104 of the first embodiment, and will not be redundantly described herein. In the step S306, the cloud data processing device 2 further defines at least one abnormal-air-quality area in the real-time air quality map 21. The abnormal-air-quality area may be, for example, in a shape of a circle, centered on the location of the pollution source and bounded by an area where the air quality is inferior to a standard value. In the step S308, the cloud data processing device 2 receives a current location CL transmitted by a client device 3. The current location CL is the GPS coordinate location of the client device 3, and is pre-set to automatically generated and automatically uploaded to the cloud data processing device 2.

In the step S310, the cloud data processing device 2 determines whether the current location CL falls within the range of the abnormal-air-quality area. If so, in the step S312, the cloud data processing device 2 generates an abnormal-air-quality notification and actively transmits the abnormal-air-quality notification to the client device 3 through a push notification. In the step S314, the client device 3 issues a warning notification based on the abnormal-air-quality notification. The warning notification can be in any form of visual clues, auditory clues or a vibration touch, alerting the user that the air quality of the current location is poor and have to avoid. Through the above steps, an escape warning effect can be achieved. For example, the carbon monoxide is colorless and odorless. Once the concentration of the carbon monoxide reaches 35 ppm in the air, it will cause damage to the human body and can even be fatal. With the method by implementing the system 100 of the present disclosure, the user can be warned to immediately avoid the current location, thereby avoiding the harmful gas.

In some embodiments, in the step S312, the cloud data processing device 2 may further perform an operation based on the real-time air quality map 21 corresponding to the user's current location CL to generate at least one evacuation route. The evacuation route represents a path from the current location CL toward an evacuation site, in which the evacuation site is out of the range of the abnormal-air-quality area and has a closest traffic distance from the current location CL. In the step S314, the cloud data processing device 2 actively transmits the abnormal-air-quality notification and the evacuation route to the client device 3 through issuing a push notification. The client device 3 displays the evacuation route on a display (not shown) via a user interface design. Through the above steps, the cloud data processing device 2 generates the evacuation route based on the updated real-time air quality map 21, which is constructed by combining the collected large-amount single-point air data SIa, SIb, and SIc with the meteorological data such as the wind direction and weather patterns. Thus, the system 100 of the present disclosure can instruct the user to leave the area contaminated by harmful gas or heavy smoke in the fire as soon as possible, and has the function to provide the escape instructions in the public accident.

In some other embodiments, in the step S314, the warning notification alerts the user to wear a mask or alerts the user to wear an oxygen supply device, such as an oxygen mask connected to an oxygen bottle.

In summary, the present disclosure provides a plurality of mobile devices each of which has an actuating and sensing module to sense single-point air quality data at its respective location and transmit the single-point air quality data to a cloud data processing device. The cloud data processing device collects the single-point air quality data from the mobile devices in a predetermined period of time, processes the single-point air quality data and generates a real-time air quality map by combining the processed single-point air quality data with geographic data and meteorological data. At this time, a client device can transmit a fixed point data of an instant location to the cloud data processing device through communication transmission and can send a request for information to the cloud data processing device. The cloud data processing device generates the information based on the real-time air quality map and the fixed point data of the instant location, and transmits the information to the client device. Moreover, the present disclosure provides a system combining the air quality data from a plurality of mobile devices and integrating other relevant data to generate the real-time air quality map. In this way, it not only makes full use of the advantages of the number and mobility of the mobile devices, but also makes the information more accurate than that of the conventional fixed-point air monitoring system. In addition, since the processed single-point air quality data of the present disclosure are further combined with the geographic information and the meteorological data, a variety of derivative information beneficial to the user can be provided. The derivative information includes a designated route, air quality information, an abnormal-air-quality notification, a warning notification, or an evacuation route. As to the prior art, the air quality information are determined by data related to a small number of fixed point locations, and it fails to provide users with the ability to actively query the air quality related to a specific location. In comparison, the present disclosure better utilizes the information with big data operations and has significant improvement in providing precise air quality information related to a specified location.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A method for providing air quality information, comprising steps of:
   (a) collecting single-point air quality data from a plurality of mobile devices in a predetermined period of time by a cloud data processing device, wherein each of the mobile devices has an actuating and sensing module to generate the single-point air quality data, and the single-point air quality data is transmitted to the cloud data processing device through communication transmission, wherein the actuating and sensing module comprises at least one actuating device and at least one sensor, in which the at least one actuating device drives air from outside the at least one actuating and sensing module to make the at least one sensor sense the air and generate the air detection data, wherein the at least one sensor is disposed adjacent to the at least one actuating device;
   (b) integrating and calculating the single-point air quality data by the cloud data processing device to obtain a first calculation result, generating a real-time air quality map by combining the first calculation result and geographic information, wherein when there is no corresponding air quality information related to a specific location, the cloud data processing device fetches the air quality information of the other locations neighboring to the specific location and calculates an average thereof, the average is further calculated with using a meteorological data as a parameter to obtain a second calculation result, and the second calculation result will be presented as the air quality information related to the specific location;
   (c) receiving a current location generated by a client device by the cloud data processing device through communication transmission;
   (d) generating information based on the current location and the real-time air quality map by the cloud data processing device; and
   (e) transmitting the information to the client device by the cloud data processing device through communication transmission.

2. The method according to claim 1, wherein the single-point air quality data comprises position data generated by the mobile device and air detection data generated by the actuating and sensing module of the mobile device.

3. The method according to claim 1, wherein the air detection data is acquired by detecting at least one selected from the group consisting of carbon monoxide, carbon dioxide, sulfur dioxide, nitrogen dioxide, suspended particle, fine suspended particle, oxygen, ozone and a combination thereof.

4. The method according to claim 1, wherein the air detection data is acquired by detecting a volatile organic compound.

5. The method according to claim 4, wherein the volatile organic compound comprises ammonia or ethanol.

6. The method according to claim 1, wherein the air detection data is acquired by detecting at least one type of target selected from the group consisting of a virus, a bacterium and a microorganism.

7. The method according to claim 1, wherein the information comprises a motion direction.

8. The method according to claim 1, wherein the step (c) further comprising a step of activating a mobile application provided on the client device and transmitting a destination inputted by operating the mobile application to the cloud data processing device through communication transmission, after which the cloud data processing device generates the information based on the real-time air quality map, the current location and the destination, wherein the information comprises at least one designated route.

9. The method according to claim 1, wherein the information is air quality information related to the current location according to the real-time air quality map.

10. The method according to claim 1, wherein the step (b) further comprises steps of combining the first calculation result with the meteorological data to generate an updated real-time air quality map, wherein the meteorological data comprises at least one selected from the group consisting of a wind direction, a wind speed, a humidity, a temperature, a weather pattern and a combination thereof.

11. The method according to claim 10, wherein the information comprises a motion direction.

12. The method according to claim 10, wherein the step (c) further comprises a step of activating a mobile application provided on the client device and transmitting a destination inputted by operating the mobile application to the cloud data processing device through communication transmission, after which the cloud data processing device generates the information based on the updated real-time air quality map, the current location and the destination, wherein the information comprises at least one designated route.

13. The method according to claim 10, wherein the information is air quality information related to the current location according to the updated real-time air quality map.

14. The method according to claim 1, wherein the information is transmitted through a push notification.

15. The method according to claim 14, wherein the step (b) further comprises a step of defining at least one abnormal-air-quality area in the real-time air quality map by the cloud data processing device, wherein when the cloud data processing device determines that the current location transmitted from the client device is located within the abnormal-air-quality area, the information transmitted from the cloud data processing device to the client device comprises an abnormal-air-quality notification, and the client device issues a warning notification based on the abnormal-air-quality notification.

16. The method according to claim 15, wherein the information comprises an evacuation route, and the evacuation route is a path from the current location toward an evacuation site out of the abnormal-air-quality area.

17. The method according to claim 15, wherein the warning notification alerts a user to wear a mask.

18. The method according to claim 15, wherein the warning notification alerts a user to wear an oxygen supply device.

19. A method for providing air quality information, comprising steps of:
(a) collecting single-point air quality data from a plurality of mobile devices in at least one predetermined period of time by at least one cloud data processing device, wherein each of the mobile devices has at least one actuating and sensing module to generate the single-point air quality data, and the single-point air quality data is transmitted to the cloud data processing device through communication transmission, wherein the actuating and sensing module comprises at least one actuating device and at least one sensor, in which the at least one actuating device drives air from outside the at least one actuating and sensing module to make the at least one sensor sense the air and generate the air detection data, wherein the at least one sensor is disposed adjacent to the at least one actuating device;
(b) integrating and calculating the single-point air quality data by the cloud data processing device to obtain a first calculation result, generating at least one real-time air quality map by combining the first calculation result and geographic information, wherein when there is no corresponding air quality information related to a specific location, the cloud data processing device fetches the air quality information of the other locations neighboring to the specific location and calculates an average thereof, the average is further calculated with using a meteorological data as a parameter to obtain a second calculation result, and the second calculation result will be presented as the air quality information related to the specific location;
(c) receiving at least one current location generated by at least one client device by the cloud data processing device through communication transmission;
(d) generating information based on the at least one current location and the real-time air quality map by the cloud data processing device; and
(e) transmitting the information to the at least one client device by the cloud data processing device through communication transmission.

* * * * *